United States Patent
Köhler et al.

(10) Patent No.: US 11,679,730 B2
(45) Date of Patent: Jun. 20, 2023

(54) METHOD FOR IDENTIFYING OCCUPANT-SPECIFIC SETTINGS AND VEHICLE FOR PERFORMING METHOD FOR IDENTIFYING OCCUPANT-SPECIFIC SETTINGS

(71) Applicant: e.solutions GmbH, Ingolstadt (DE)

(72) Inventors: Thomas Köhler, Nuremberg (DE); Matthias Stock, Heroldsbach (DE)

(73) Assignee: E.SOLUTIONS GMBH, Ingolstadt (DE)

( * ) Notice: Subject to any disclaimer, the term of this patent is extended or adjusted under 35 U.S.C. 154(b) by 483 days.

(21) Appl. No.: 16/697,739

(22) Filed: Nov. 27, 2019

(65) Prior Publication Data
US 2020/0180534 A1 Jun. 11, 2020
US 2023/0148445 A9 May 11, 2023

(30) Foreign Application Priority Data
Dec. 11, 2018 (EP) .................................... 18211653

(51) Int. Cl.
*B60R 16/037* (2006.01)
*A61B 5/1171* (2016.01)
(Continued)

(52) U.S. Cl.
CPC .......... *B60R 16/037* (2013.01); *A61B 5/1171* (2016.02); *A61B 5/1172* (2013.01);
(Continued)

(58) Field of Classification Search
CPC ... B60R 16/037; A61B 5/1171; A61B 5/1172; A61B 5/1176; G06V 40/12; G06V 40/16;
(Continued)

(56) References Cited

U.S. PATENT DOCUMENTS 10,850,693 B1* 12/2020 Pertsel .................. G05D 1/0088
10,953,850 B1* 3/2021 Pertsel .................... G06N 3/08
(Continued)

FOREIGN PATENT DOCUMENTS

DE 102005021171 A1 11/2006
DE 102014111271 A1 2/2015
(Continued)

*Primary Examiner* — John B Strege
(74) *Attorney, Agent, or Firm* — Tarolli, Sundheim, Covell & Tummino L.L.P

(57) ABSTRACT

A method for identifying occupant-specific settings for a vehicle comprises detecting a vehicle occupant; collecting biometric occupant data of the detected vehicle occupant; assembling a descriptor based on at least part of the collected occupant data; storing the descriptor in a database; and updating a cluster of descriptors in the database based on the assembled descriptor, wherein descriptors grouped in the cluster are close to each other, and wherein the cluster corresponds to the detected vehicle occupant. Based on the cluster and assembled descriptor can be assigned to the cluster, and vehicle setting data can be calculated that has been stored in association with the cluster. The vehicle setting data corresponds to occupant-specific settings for the vehicle. A vehicle comprises a system capable of performing such method.

13 Claims, 5 Drawing Sheets

Figure 1:
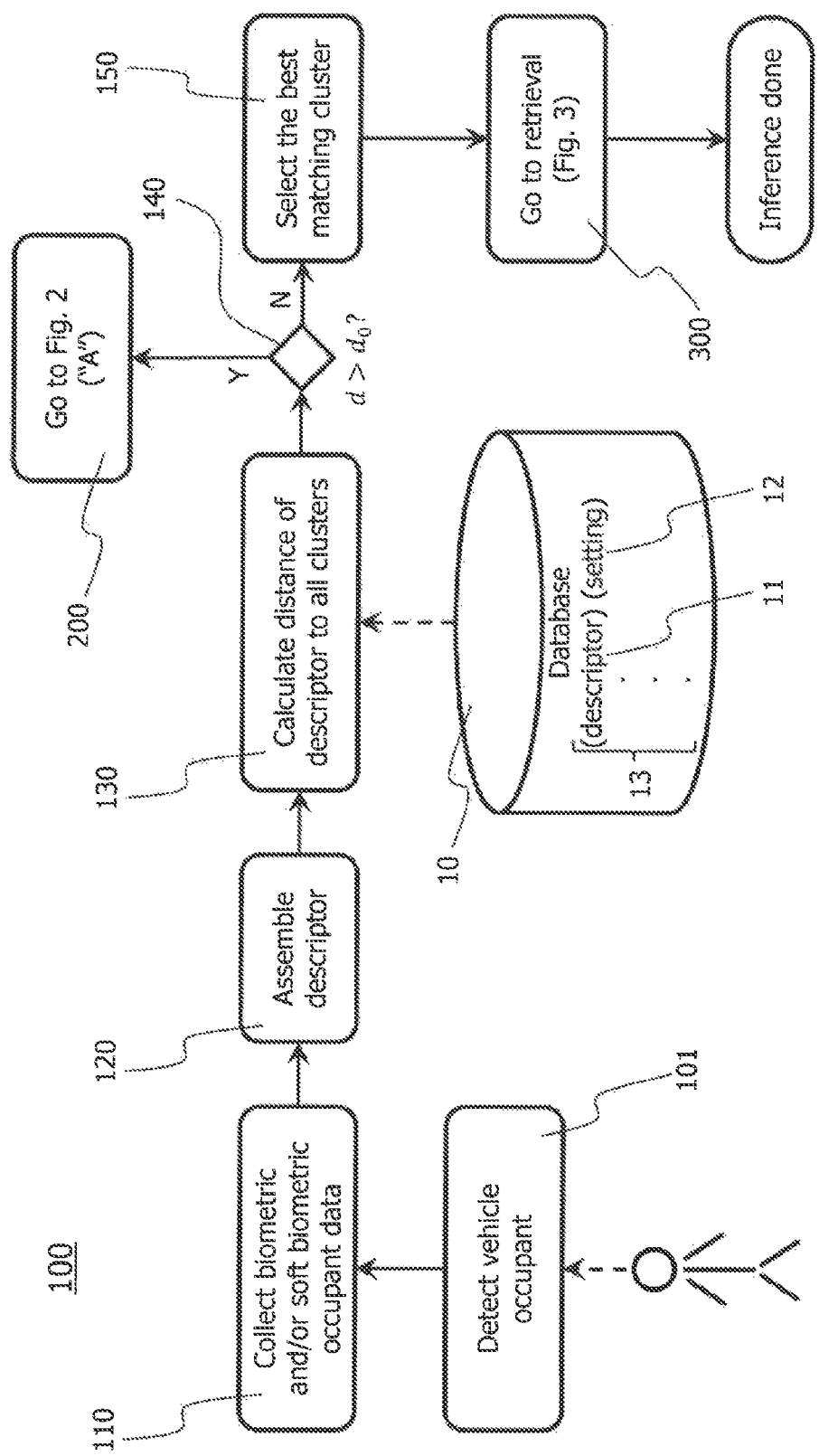

(51) Int. Cl.
- *A61B 5/1172* (2016.01)
- *G10L 17/04* (2013.01)
- *G10L 17/00* (2013.01)
- *G06V 40/12* (2022.01)
- *G06V 40/16* (2022.01)
- *G06V 40/18* (2022.01)
- *G06V 40/70* (2022.01)

(52) U.S. Cl.
CPC ............ *A61B 5/1176* (2013.01); *G06V 40/12* (2022.01); *G06V 40/16* (2022.01); *G06V 40/18* (2022.01); *G06V 40/70* (2022.01); *G10L 17/00* (2013.01); *G10L 17/04* (2013.01)

(58) Field of Classification Search
CPC ........ G06V 40/18; G06V 40/70; G06V 20/59; G10L 17/00; G10L 17/04; G06K 9/6218; G06K 9/6288; G06N 20/00
See application file for complete search history.

(56) References Cited

U.S. PATENT DOCUMENTS

| | | | |
|---|---|---|---|
| 11,040,619 B1* | 6/2021 | Martin | G06T 7/593 |
| 2003/0204290 A1* | 10/2003 | Sadler | G06V 40/10 701/1 |
| 2011/0237186 A1* | 9/2011 | Preissinger | B60R 16/037 455/41.1 |
| 2014/0195477 A1 | 7/2014 | Graumann et al. | |
| 2019/0332902 A1* | 10/2019 | Gallagher | B60R 25/25 |
| 2020/0334453 A1* | 10/2020 | Thomas | B60R 21/01512 |
| 2021/0382016 A1* | 12/2021 | Jauriqui | G01N 29/04 |

FOREIGN PATENT DOCUMENTS

| | | |
|---|---|---|
| DE | 102015207774 A1 | 11/2016 |
| DE | 102016008339 A1 | 2/2017 |
| WO | 2013101054 A1 | 7/2013 |
| WO | 2015022838 A1 | 2/2015 |

* cited by examiner

METHOD FOR IDENTIFYING OCCUPANT-SPECIFIC SETTINGS AND VEHICLE FOR PERFORMING METHOD FOR IDENTIFYING OCCUPANT-SPECIFIC SETTINGS

RELATED APPLICATIONS

The present invention is a Nonprovisional Application under 35 USC 111(a), claiming priority to Serial No. EP 18211653.3-1132, filed on 11 Dec. 2018, the entirety of which are incorporated herein by reference.

The present invention relates to a method for identifying occupant-specific settings for a vehicle and a vehicle capable of performing such method. In particular, the present invention relates to a method for identifying occupant-specific settings in an unsupervised manner and a vehicle capable of performing such method.

Some vehicles are provided with the capability of adjusting particular vehicle settings, such as a seat position, steering wheel position, mirror position, etc., based on a stored setting. Such stored setting can be based on a user identity, so that multiple occupants (driver and/or passenger) can customize particular vehicle items.

The identification of vehicle occupants is conventionally determined on the basis of an unambiguous identity of the occupant. For instance, the identity of the occupant is determined based on a pre-registered device, such as a key, a token or mobile telephone, or based on a pre-registered user profile identifiable by a name, password, etc., or based on inalterable biometric data, such as a fingerprint, iris, speech, etc. Such an identification system requires a supervised learning phase, during which an occupant account is created and stored in a vehicle system.

It is an object of the present invention to provide a more efficient way of identifying occupant-specific settings for a vehicle.

This object is solved by a method as defined in independent claim 1, and a vehicle as defined in independent claim 12. Preferred embodiments are defined by the dependent claims.

A method for identifying occupant-specific settings for a vehicle comprises the steps of detecting a vehicle occupant, such as a driver or passenger, and collecting biometric occupant data of the detected vehicle occupant. The detecting of a vehicle occupant is directed to the detecting of a presence of the vehicle occupant, but does not include detecting an identification of a particular vehicle occupant. For instance, the method does not require detecting a particular vehicle occupant on the basis of unique occupant data, such as a key or (RFID-) token.

The method further comprises (once the presence of a vehicle occupant is detected and/or another event has triggered the collection of biometric occupant data) assembling a descriptor based on at least part of the collected occupant data, storing the descriptor in a database, and updating a cluster of descriptors in the database based on the assembled descriptor. A descriptor stores at least one feature, such as a biometric feature, numerically, and in case of multiple features of the vehicle occupant, the descriptor stores and combines the different features numerically as a vector. The descriptors grouped in the cluster are close to each other, e.g. have a distance below a predefined threshold, and the cluster corresponds to the detected vehicle occupant. In other words, the database holds (stores) at least two descriptors that can be compared with one another. If two or more descriptors are close to each other these descriptors can be grouped together in a cluster representing the detected vehicle occupant.

Thus, the database can further store a plurality of clusters, i.e. a plurality of descriptors grouped in two or more clusters representing two or more vehicle occupants, respectively. This provides for identifying vehicle occupants in an unsupervised manner, since there is no requirement for inputting personal information in a preceding user profile setup. New or unknown vehicle occupants can be identified "on-the-fly", i.e. without initial user profile setup, simply by supplementing an additional cluster in the database starting with a descriptor having a distance exceeding the predefined threshold to each descriptor already in the database. This allows for vehicle occupant identification without distracting the occupant, in particular a driver of the vehicle. In addition, the biometric data of the vehicle occupant may be of a rather general type. For instance, it is not required that the vehicle occupant operates a particular sensor device, such as a fingerprint sensor, and iris sensor, etc. due to the collection of different features of the vehicle occupant and storing multiple descriptors of the same vehicle occupant in a cluster. This further allows identification of the vehicle occupant without a single unambiguous or unique biometric feature.

The numerical interpretation of the biometric and/or other feature(s) of and relating to the vehicle occupant may include the storing of sensor value data, such as weight, height (relative to a fixed object in the vehicle, such as a back rest of the seat) and safety belt length, and/or the storing of calculated data based on sensor data, such as an average hair colour, skin colour, colour of the iris or the like, the curvature of an outline of the occupant's torso, specific features of the occupant's voice, etc. In addition or alternatively, a descriptor may include data based on captured three-dimensional (3D) images, such as a 3D geometry and/or topography of a head, face, extremity, torso, etc. of the vehicle occupant. For instance, the descriptor can include data representing a distance of the eyes, distance(s) of eye(s) and nose and/or ears, a size of an ear, volume of the head and/or an extremity, etc. It is to be understood that the descriptor may further store biometric data of or derived from a fingerprint sensor and/or an iris sensor.

Additionally and/or alternatively, a descriptor may include data-driven features like embeddings calculated by artificial neural networks and/or related machine learning methods applied on (sensor) data representing the vehicle occupant's face, body, speech, etc.

In an implementation variant the updating of a cluster of descriptors may comprise calculating a distance between the assembled descriptor and at least one further descriptor stored in the database, and associating the assembled descriptor with a cluster defined by the at least one further descriptor, if the distance falls below a predefined threshold or a threshold evaluated (learned) over time by the system. In other words, a cluster may already exist in the database that groups the at least one further descriptor, so that each of the further descriptors of the cluster can be used to identify the cluster. In the descriptor space distances between descriptors can be computed using any suitable distance measure, for example, calculating a Euclidean distance, a geodesic distance, etc. Thus, occupants of the vehicle may be identified by analysing distances of the descriptor(s) representing a specific occupant to descriptor(s) representing another occupant, for example by finding best matches with minimum distances in the descriptor space. The distance between descriptors may be calculated on a feature basis constituting the descriptor. In other words, a distance between descriptors is calculated on the basis of distances between corresponding features in the descriptors. Thus, a vehicle occupant may still be identified, even if the feature changes, such as hair colour.

In addition or alternatively, a distance between the assembled descriptor and an averaged descriptor representing an average of all descriptors of the cluster may be calculated and compared with the predefined threshold. This avoids increasing the "size" of the cluster, i.e. avoids a distance between two descriptors of the same cluster that exceeds a multiple of the predefined distance. This reduces the calculation of false positives, i.e. identification of an alleged vehicle occupant due to an oversized cluster, due to a deviation of the descriptors in one cluster from a mean value (average) being too large.

In the present disclosure reference is made to a distance between descriptors and/or between a descriptor and a mean (average) value of the cluster. It is to be understood that instead of or in addition to a distance the method may also rely on a similarity measure (the similarity of descriptors) and/or probability measure (a probability that two descriptors represent the same vehicle occupant). Thus, a close similarity and a high probability would be employed as is a small distance.

Furthermore, associating the assembled descriptor with the cluster may comprise storing a cluster identification for or with the descriptor (for example supplementing the descriptor with a cluster identification) and/or storing descriptor identifications of all descriptors constituting the cluster, such as storing a mapping table of descriptors and clusters.

In another implementation variant the biometric occupant data comprises strong biometric data and/or soft biometric data. A differentiation between strong and soft biometric data allows reliable identification of a particular vehicle occupant, even if a change of the soft biometric data of the same occupant is monitored, due to storing such changes in the cluster representing the occupant over time. For instance, strong biometric data may include facial feature data (e.g., geometric features of a face of the occupant), speech data, iris data and/or fingerprint data. The strong biometric data can be unique to the occupant, such as iris and fingerprint data. The soft biometric data may include body weight data, body height data and/or safety belt length data. The safety belt length data may depend on a body height of the occupant and, hence, represents soft biometric data, which may change or vary over time.

The method is not relying only on strong biometric data, since vehicle occupant identification is based on the entire descriptor. Even if a particular biometric data item may not be derived, a descriptor can still be stored and clustered, since it provides an identification of the vehicle occupant. Due to the multiplicity of descriptors clustered to identify a vehicle occupant a reliable identification is possible, even without strong biometric data. According to a further variant, a descriptor may be discarded, if its distance to other descriptors in the database exceeds the (predefined or learned) threshold and/or the number of features or types of biometric data available at the time the descriptor is assembled and/or stored falls below another threshold.

Thus, instead of requiring a unique identification (such as a token or key) an occupant of the vehicle may be identified based on a variety of features describing the occupant. Furthermore, an identity of the occupant, such as a name, age, sex, etc. is not required which avoids problems of data protection. In other words, although the vehicle occupant can be identified, the information is anonymized as it does not comprise any personal information about the vehicle occupant.

The data constituting a descriptor may include all collected biometric occupant data or, alternatively, may include a subset of the collected biometric occupant data. For instance, based on a predefined setting of the method, only soft biometric data may be used to assemble a descriptor, only strong biometric data may be used to assemble a descriptor, only some features of the strong and/or soft biometric data may be used to assemble a descriptor. In other words, a vehicle occupant is modelled by a descriptor numerically by combining different features as a vector. These features may be based on real sensor measurement data or abstract mathematical descriptions thereof. The combination of multiple features, i.e. the use of multiple biometric occupant data, to assemble a descriptor provides for more discriminative descriptors of the vehicle occupant.

According to a variant, at least the steps of collecting biometric occupant data, assembling a descriptor, storing the descriptor, and updating the cluster of descriptors may be performed automatically without user initiation and/or user intervention. For instance, performing these steps can be triggered by a system of the vehicle at particular time points, such as the beginning of a journey, the start of an engine of the vehicle, in certain time intervals (e.g., once per hour, once a day, once a week, etc.), and/or when a state of the vehicle changes, such as when a door is opened and/or closed, when a safety belt is buckled, and/or when a signal of a weight sensor in a seat of the vehicle changes and/or indicates a change of weight above a (predefined) threshold.

In a further implementation variant a cluster algorithm for clustering the assembled descriptors can be selected. For instance, a cluster algorithm can be chosen on the basis of pre-set task settings. According to a first setting, if the number of occupants and, hence, the number of clusters is known or predictable, a centroid-based approach is used, such as a k-means approach. According to a second setting, if the number of vehicle occupants and, hence, the number of clusters are unknown and arbitrary large, for example in a vehicle of a large fleet used by a plurality of drivers, a hierarchical clustering is used.

In yet a further implementation variant, the clustering (cluster algorithm) is triggered by certain events. For instance, after collecting/assembling a predefined number of descriptors, the clustering is updated. The predefined number may be 1, but in an alternative implementation may be greater than 1, such as after collecting/assembling 5 descriptors or after collecting/assembling 10 descriptors. In addition or alternatively, the clustering may be updated after the vehicle occupant adjusted a particular vehicle setting, such as adjusting a seat position, adjusting a mirror, or the like.

According to another variant the method may further comprise associating the descriptor with at least one current vehicle setting. For instance, storing the descriptor may comprise storing the descriptor in association with the at least one vehicle setting. The storing may take place in the same database where the descriptor(s) and clusters are stored. A vehicle setting may relate to any item in the vehicle that can be adjusted and/or personalized, such as the position of a seat, the position of a back rest, the position of a head rest, the position of a mirror, the position of a steering wheel, the position of a safety belt holder or deflector, the temperature and/or volume flow of an air conditioning system, a radio and/or TV station or other setting of an infotainment system, etc.

According to another implementation variant, the method may further comprise calculating a distance of the assembled descriptor to each cluster in the database, and comparing the calculated distance with a threshold value, such as a predefined threshold. The distance between the descriptor and cluster may be based on an average for each feature of the descriptors constituting the cluster. In other words, the assembled descriptor is compared to an average description of the vehicle occupant represented by the cluster. The distance may be calculated on a feature-by-feature basis.

If the calculated distance exceeds the threshold value, it is assumed that the detected occupant of the vehicle is unknown to the system. In this case, the method comprises storing the assembled descriptor in association with a new cluster representing a new vehicle occupant. Alternatively, the assembled descriptor may be stored in association with a cluster for unknown descriptors, which will be evaluated at a later time point, such as a time when two unknown clusters having a distance below the threshold value are assembled and stored. In any case, a learning phase of the system is initiated, in which a new occupant is described via descriptors and vehicle settings are stored for the new occupant. Alternatively, the descriptor may be discarded, for example, if the number of features (number of biometric data) available for this respective descriptor falls below a predefined threshold.

Furthermore, the method also comprises, if the calculated distance does not exceed the threshold value, selecting the best matching cluster stored in the database, and calculating a vehicle setting based on the best matching cluster. In other words, the best matching cluster represents the vehicle occupant that has been identified via the assembled descriptor, i.e. that has been identified as a particular occupant on a particular seat of the vehicle.

Once calculated, the calculated vehicle setting can be used to adjust at least one vehicle item. Thus, once a particular occupant has been detected and identified via the assembled descriptor and the clusters stored in the database (in form of a matching cluster and not a specific identification as in conventional systems), a vehicle item can automatically be adjusted on the basis of vehicle setting information stored for the best matching cluster, i.e. for the particular occupant.

Calculating a vehicle setting may be based on any function deriving an optimum vehicle setting for the particular occupant. According to a variant, calculating a vehicle setting comprises retrieving at least one cluster item of the best matching cluster from the database, i.e. at least one cluster item stored in association with the best matching cluster in the database. Each cluster item may include at least one vehicle setting. The calculating of a vehicle setting may further comprise calculating at least one occupant-specific vehicle setting based on the at least one vehicle setting of the retrieved at least one cluster item. In other words, a cluster item associated with the particular cluster may be a feature vector representing the setting of one or more vehicle items in association to the particular cluster. The association to a particular cluster specifies an occupant-specific vehicle setting of the particular vehicle item identified by the cluster item.

According to a further variant, the calculating of at least one occupant-specific vehicle setting comprises determining a latest stored vehicle setting, such as a last tuned radio and/or TV station, calculating an average or median or mode of a predefined (or predetermined) number of vehicle settings of the retrieved at least one cluster item, such as an average seat position or median or mode of seat positions, an average mirror position or median or mode of mirror positions, an average temperature setting or median or mode of temperature settings, etc., and/or determining a vehicle setting based on sensor data, such as selecting an air conditioning setting out of a plurality of stored air conditioning settings (from stored cluster items) depending on a current temperature measurement (in this case the cluster items have to be stored together with a temperature measurement when the particular air conditioning setting was set and stored). The mode of vehicle settings is a particular setting having the highest number of occurrences in the retrieved at least one cluster item.

The cluster item(s) may be stored each time a descriptor is assembled and/or a descriptor is stored in the database. Thus, not only the vehicle occupant is monitored over time, in order to develop a cluster of descriptors representing the vehicle occupant, but also the vehicle setting(s) is/are monitored over time. As with the descriptors representing the vehicle occupant, the vehicle setting(s) may be stored in a descriptor, which is clustered and associated with the cluster representing the vehicle occupant. Thus, vehicle item(s) can be set not only in accordance with the particular vehicle occupant, but also in accordance with further influencing factors, such as outside temperature, rain, sunshine, speed of travel, type of road currently being used, etc.

According to a further aspect, a computer-readable medium is configured to store executable instructions that, when executed by a processor, cause the processor to perform the method according to one of the disclosed (implementation) variants. The computer-readable medium can be any volatile or non-volatile storage medium.

According to yet a further aspect, a vehicle comprises a processor, a storage device including a database, and at least one adjustable vehicle item configured to assume a particular setting. The processor is configured to perform the method according to one of the disclosed (implementation) variants.

The vehicle may further comprise at least one sensor configured to sense the biometric occupant data. The at least one sensor may optionally comprise a camera, a microphone, a weight sensor, and/or a fingerprint sensor. The vehicle may additionally comprise at least one sensor configured to sense an ambient feature of the vehicle, such as the temperature sensor, a water sensor, a vibration sensor, a gyroscope, etc. Such ambient feature detected by the additional sensor(s) can be used by the processor to calculate a vehicle setting based on ambient influencing factors.

In an implementation variant the processor is further configured to initiate the method according to one of the disclosed (implementation) variants each time the vehicle starts a journey.

The present disclosure is not restricted to the described aspects, variants, implementation variants and alternatives, but combinations of the described aspects, variants, implementation variants and alternatives our possible and fall under the present disclosure.

Figure 2:
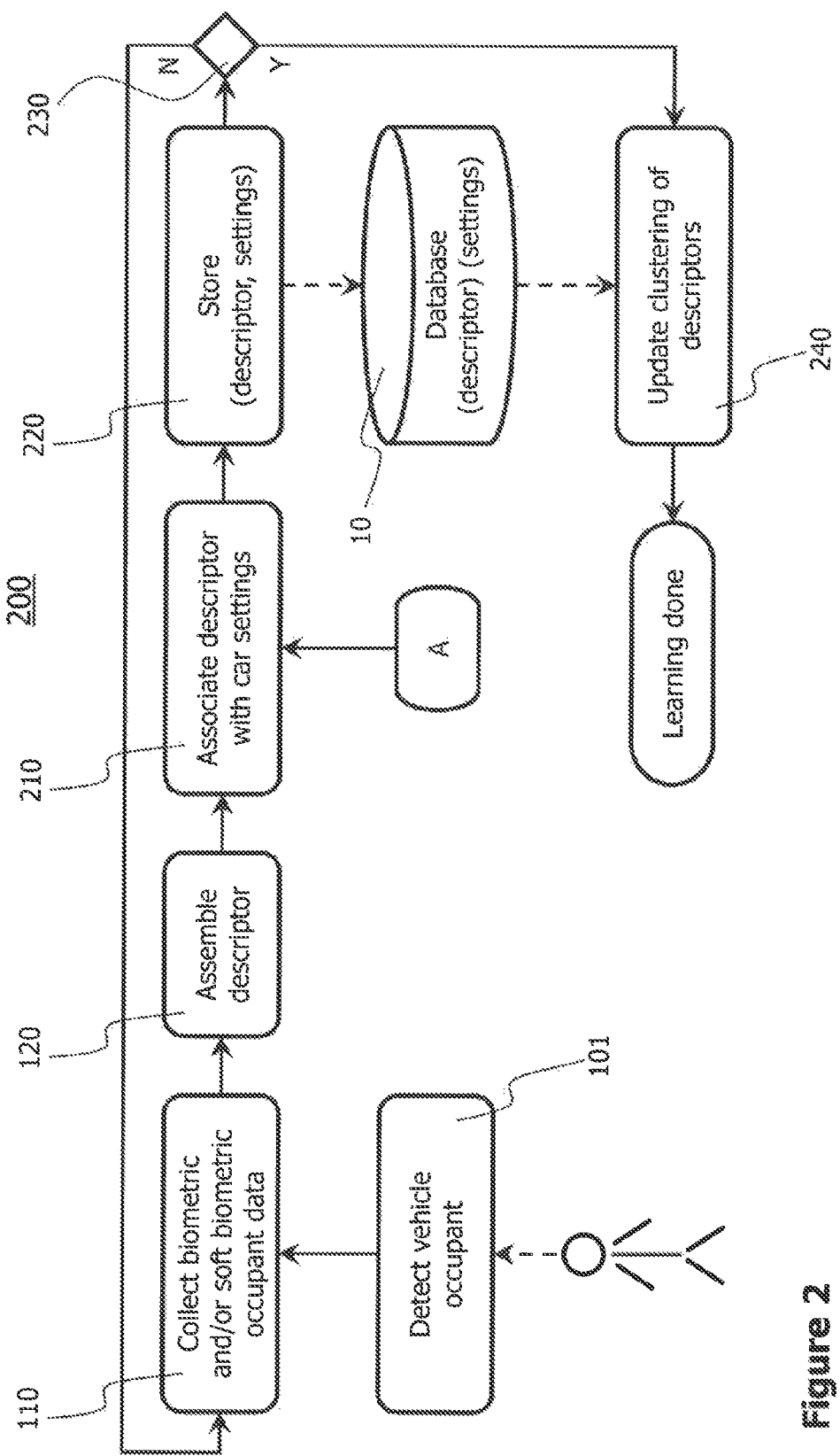
Figure 3:
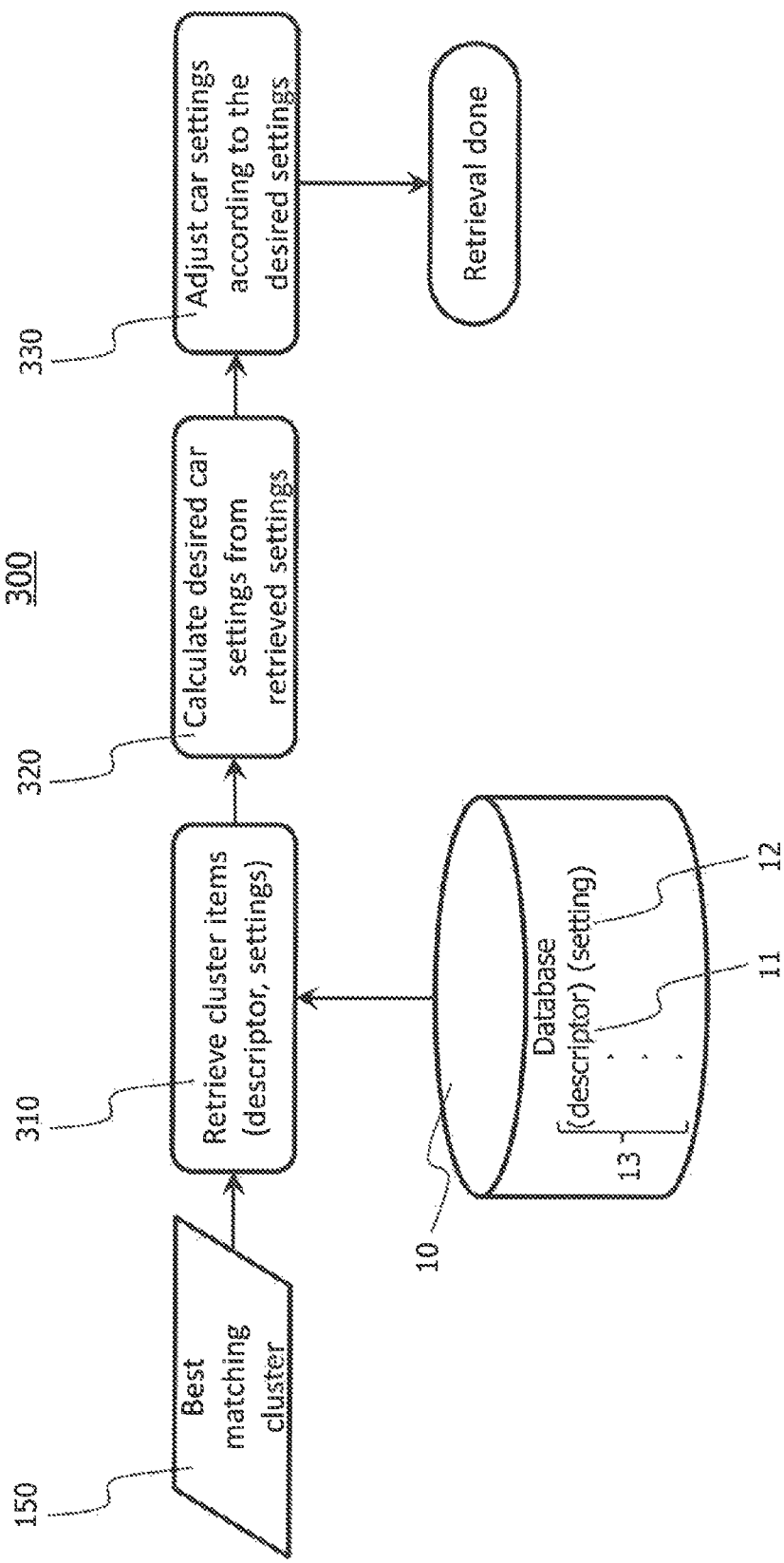
Figure 4:
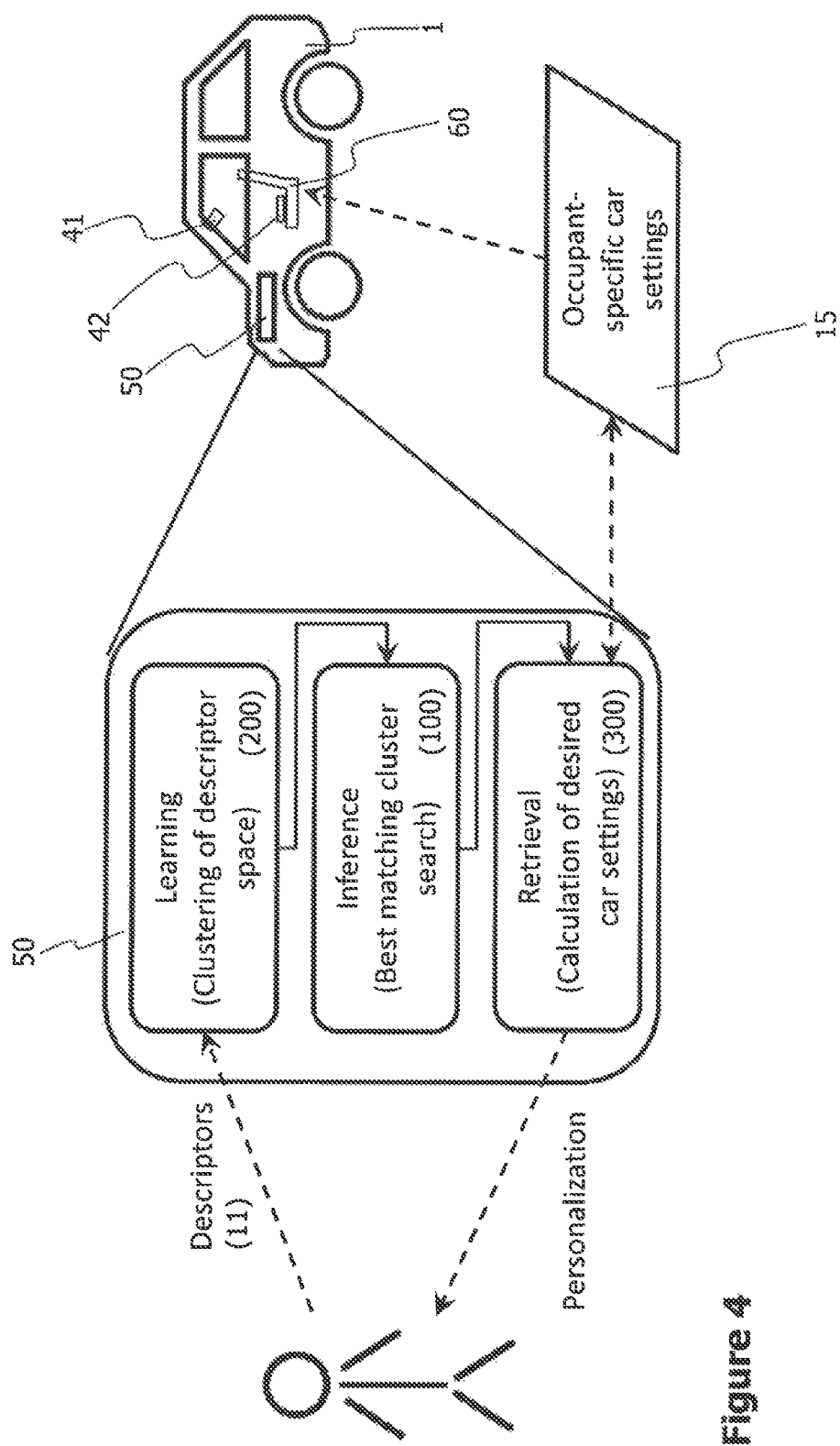

Preferred examples for understanding the disclosed method for identifying occupant-specific settings for a vehicle and corresponding vehicle are described in greater detail with reference to the attached schematic drawings in the following, wherein FIG. 1 depicts a schematic flow diagram of an inference phase for identifying a best matching cluster representing a detected vehicle occupant, FIG. 2 depicts a schematic flow diagram of a learning phase for assembling and storing a descriptor describing the detected vehicle occupant, FIG. 3 depicts a schematic flow diagram of the retrieval phase for retrieving occupant-specific settings for a vehicle, FIG. 4 schematically illustrates a vehicle comprising a system capable of performing a method according to the phases of FIGS. 1 to 3, and FIG. 5 schematically illustrates a descriptor used for describing the detected vehicle occupant.

FIG. 1 depicts a schematic flow diagram of an inference phase 100 for identifying a best matching cluster representing a detected vehicle occupant. The inference phase 100 assumes that a database 10 already holds vehicle occupant-specific data, such as data 11 representing the occupant and data 12 representing vehicle settings. In step 101 a vehicle occupant is detected, for example due to the change of a sensor signal, such as a camera 41 or microphone 41 and/or a weight sensor 42 (see FIG. 4).

Once the vehicle occupant is detected (or alternatively a different event triggers the inference phase 100, such as the change of an ambient feature detected by an ambient sensor (not shown)), biometric data of the detected vehicle occupant is collected (step 110). The collection of this data may include strong and/or soft biometric occupant data, which is further used to assemble a descriptor 11 in step 120. Assembling a descriptor 11 can include the calculation of feature values to be stored as descriptor items as will be described with respect to FIG. 5.

The method then calculates (130) a distance "d" of the assembled descriptor 11 to clusters 13 retrieved from database 10. The clusters 13 are a group of descriptors 11 having a distance to one another falling below a predefined threshold, so that a cluster 13 represents a vehicle occupant. In step 140 it is determined whether the calculated distance of descriptor 11 to cluster(s) 13 exceeds a predefined threshold $d_0$ or not.

If the distance of the descriptor 11 to a particular cluster 13 does not exceed the threshold value, a best matching cluster 13 is selected in step 150. The selection of the best matching cluster 13 may include selecting a cluster 13 having the smallest distance to the assembled descriptor 11. In other words, the best matching cluster 13 represents a vehicle occupant that has been identified on the basis of descriptor 11 data and cluster 13 data stored in database 10. Based on the best matching cluster 13 a retrieval phase 300 is started.

If the distance "d" of the assembled descriptor 11 to each cluster 13 stored in database 10 exceeds the predefined threshold $d_0$, a learning phase 200 schematically illustrated in FIG. 2 is started. Alternatively, the learning phase 200 may be started when detecting 101 a vehicle occupant, i.e. may be started due to the same trigger initiating the inference phase 100. Furthermore, the detecting 101 of a vehicle occupant may be based on the same evaluations as described with respect to the inference phase 100.

Likewise, the collecting 110 of biometric occupant data and the assembling 120 of a descriptor 11, may correspond to the steps of the inference phase 100. For instance, when the learning phase 200 is initiated from step 140 of the inference phase 100, the method may directly start (at point "A") with step 210, i.e. associating the assembled descriptor 11 with one or more car settings 12. The associating 210 of the assembled descriptor 11 with one or more car settings 12 may be based on the car settings 12 as set at the time of assembling the descriptor 11 or storing 220 the descriptor 11 in database 10.

Alternatively, the associating 210 of the descriptor 11 with car settings 12 may be skipped and the method (starts with or) proceeds with step 220, i.e. storing (only) the descriptor 11 in database 10. This may be useful, if a new (empty) database 10 not holding any or many descriptors 11, so that the database 10 is first filled with descriptors 11 describing one or more vehicle occupants, before personalized car settings 12 are stored for the vehicle occupants represented by the stored descriptors 11.

For instance, in step 230 a determination may be made whether the learning phase 200 shall be continued or whether the stored (220) descriptors 11 shall be further evaluated and/or analysed. Thus, the method may repeat beginning at step 110, i.e. collecting biometric occupant data. Otherwise, the method may continue with step 240, i.e. updating clusters 13 (or clustering) of the assembled and stored descriptors 11. A cluster 13 is used to group descriptors 11, which are close to each other, i.e. that have a distance between one another falling below a predefined threshold (such as threshold $d_0$). Alternatively, descriptors 11 having a distance to an average or median or mode of the cluster 13 falling below the predefined threshold (e.g., $d_0$) are grouped in the cluster 13. Thus, a cluster 13 corresponds to the detected vehicle occupant and describes features of the vehicle occupant.

FIG. 3 depicts a schematic flow diagram of the retrieval phase 300 for retrieving occupant-specific settings 15 for a vehicle 1. The retrieval phase 300 starts with a best matching cluster 13, such as the one selected in step 150 (FIG. 1). Based on the best matching cluster 13 at least one cluster item is retrieved from database 10 in step 310, wherein each cluster item includes at least one vehicle setting 12.

Thereafter, a (desired) vehicle setting is calculated 320 from the retrieved cluster item(s), i.e. from the retrieved setting(s). The calculating 320 of at least one occupant-specific vehicle setting 15 can comprise determining the latest stored vehicle setting 12, calculating an average of a predefined number of vehicle settings 12 of the retrieved at least one cluster item, and/or determining a vehicle setting 12 based on sensor data, such as data of sensors detecting ambient features.

Once the desired vehicle setting(s) is/are calculated (step 320), the corresponding vehicle item(s), such as a vehicle seat 60 (FIG. 4), is/are adjusted in step 330 to the calculated vehicle setting(s). The retrieval phase 300 is then terminated.

FIG. 4 schematically illustrates a vehicle 1 comprising a system 50 capable of performing a method according to one or more of the inference phase 100, learning phase 200, and retrieval phase 300. The system 50 may be a processor and may further include a database 10 capable of storing descriptors 11, vehicle settings 12 and clusters 13. Furthermore, the system 50 may also include a storage device, such as a computer-readable medium, configured to store executable instructions that, when executed by a processor perform one or more of the phases 100, 200, 300.

The system 50 may be part of the vehicle 1, for example may be integrated into an electronic control unit (ECU) forming part of the vehicle 1.

In addition, the vehicle may further include at least one sensor 41, 42 configured to sense biometric occupant data. FIG. 4 exemplarily depicts a camera or microphone 41 and a weight sensor 42 installed in or on a seat 60 of the vehicle 1. The seat 60 further illustrates an exemplary vehicle item that can be adjusted or personalized for the detected vehicle occupant. In other words, occupant-specific vehicle settings 15 may be retrieved in the retrieval phase 300 and may be used, for example by processor system 50 to adjusted a setting of the vehicle item 60.

Figure 5:
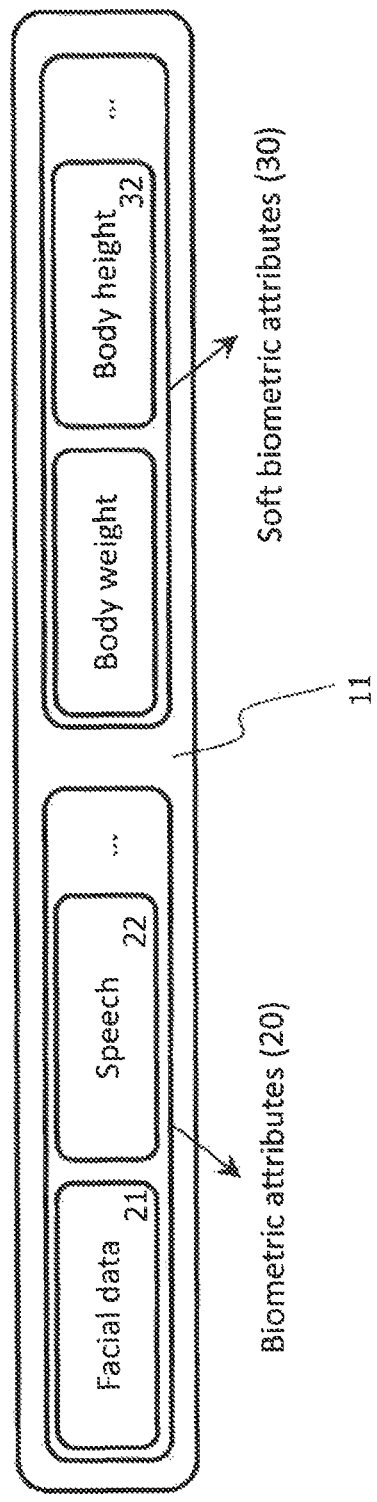

FIG. 5 schematically illustrates a descriptor 11 used for describing the detected vehicle occupant. The data stored in and/or with the descriptor 11 may comprise (strong) biometric data (biometric attributes) 20 as well as soft biometric data (of biometric attributes) 30. The (strong) biometric data 20 can include facial feature data 21, speech data 22, iris data and/or fingerprint data, while the soft biometric data 30 can include weight data 31 of a body of the occupant, body height data 32 and/or safety belt length data.

A data structure similar to the descriptor 11 can be used for storing the vehicle settings 12. In other words, a similar descriptor can be stored in database 10 containing data and data values representing the setting of particular vehicle items, such as any item in the vehicle that can be adjusted or personalized for the respective occupant, in association with a descriptor 11 and/or in association with a cluster 13.

The invention claimed is:

1. A method for identifying occupant-specific settings for a vehicle, the method comprising:
   detecting a presence of vehicle occupant without detecting an identification of a particular vehicle occupant;
   collecting biometric occupant data of the detected vehicle occupant;
   assembling a descriptor based on at least part of the collected occupant data;
   storing the descriptor in a database;
   updating a cluster of descriptors in the database based on the assembled descriptor, wherein descriptors grouped in the cluster are close to each other, and wherein the cluster corresponds to the detected vehicle occupant;
   calculating a distance of the assembled descriptor to each cluster in the database;
   comparing the calculated distance with a threshold value; and
   if the calculated distance does not exceed the threshold value:
      selecting the best matching cluster stored in the database; and
      calculating a vehicle setting based on the best matching cluster
   wherein calculating a vehicle setting comprises:
      retrieving at least one cluster item of the best matching cluster from the database, each cluster item including at least one vehicle setting, and
      calculating at least one occupant-specific vehicle setting based on the at least one cluster item.

2. The method according to claim 1, wherein updating a cluster of descriptors comprises calculating a distance between the assembled descriptor and at least one further descriptor stored in the database, and/or associating the assembled descriptor with a cluster defined by the at least one further descriptor, if the distance falls below a predefined threshold.

3. The method according to claim 1, wherein the biometric occupant data comprises strong biometric data, in particular facial feature data, and/or speech data, and/or soft biometric data, in particular body weight data, body height data and/or safety belt length data.

4. The method according to claim 1, wherein at least the steps of collecting biometric occupant data, assembling a descriptor, storing the descriptor, and updating the cluster of descriptors are performed automatically without user initiation and/or user intervention.

5. The method according to claim 1, further comprising: associating the descriptor with at least one current vehicle setting, wherein storing the descriptor comprises storing the descriptor in association with the at least one vehicle setting.

6. The method according to claim 1, wherein the selecting of the best matching cluster includes selecting a cluster having the smallest distance to the assembled descriptor.

7. The method according to claim 1, further comprising: adjusting at least one vehicle item based on the calculated vehicle setting.

8. The method according to claim 1, wherein calculating at least one occupant-specific vehicle setting comprises:
   determining a latest stored vehicle setting,
   calculating an average of a predefined number of vehicle settings of the retrieved at least one cluster item,
   calculating a median of a predefined number of vehicle settings of the retrieved at least one cluster item,
   calculating a mode of a predefined number of vehicle settings of the retrieved at least one cluster item, and/or
   determining a vehicle setting based on a sensor data.

9. A non-transitory computer-readable medium configured to store executable instructions that, when executed by a processor, cause the processor to perform the method according to claim 1.

10. A vehicle comprising: a processor; a storage device including a database; and at least one adjustable vehicle item configured to assume a particular setting, wherein the processor is configured to perform the method according to claim 1.

11. The vehicle according to claim 10, further comprising: at least one sensor configured to sense the biometric occupant data.

12. The vehicle according to claim 11, wherein the at least one sensor comprises a camera, a microphone, and/or a weight sensor.

13. The vehicle according to claim 10, wherein the processor is further configured to detect a vehicle occupant; collect biometric occupant data of the detected vehicle occupant; assemble a descriptor based on at least part of the collected occupant data ; store the descriptor in a database; and update a cluster of descriptors in the database based on the assembled descriptor, wherein descriptors grouped in the cluster are close to each other, and wherein the cluster corresponds to the detected vehicle occupant, each time the vehicle starts a journey.

* * * * *